United States Patent [19]

Johnson

[11] Patent Number: 4,861,900

[45] Date of Patent: Aug. 29, 1989

[54] PURIFICATION AND HYDROGENATION OF SULFOLENES

[75] Inventor: Marvin M. Johnson, Bartlesville, Okla.

[73] Assignee: Phillips Petroleum Company, Bartlesville, Okla.

[21] Appl. No.: 864,047

[22] Filed: May 16, 1986

[51] Int. Cl.$^4$ .......................................... C07D 333/48
[52] U.S. Cl. ..................................................... 549/87
[58] Field of Search .......................................... 549/87

[56] References Cited

U.S. PATENT DOCUMENTS

| | | | |
|---|---|---|---|
| 3,152,144 | 10/1964 | Middlebrook | 260/332.1 |
| 3,252,997 | 5/1966 | Riddevikhoff et al. | 260/332.1 |
| 3,345,384 | 10/1967 | Oelderik et al. | 260/332.1 |
| 3,417,103 | 12/1968 | Warner | 260/332.1 |
| 3,622,598 | 11/1971 | Willis | 260/332.1 |
| 3,928,385 | 12/1975 | Huxley | 260/332.1 |
| 4,188,327 | 2/1980 | Kubicek | 549/87 |
| 4,286,099 | 8/1981 | Nash et al. | 549/87 |

FOREIGN PATENT DOCUMENTS 0220267  5/1983  U.S.S.R. ................................. 549/87

OTHER PUBLICATIONS

Maeda Chem Abst 49433b, vol 76 (1972).
Hoppe Chem Abst 174532b, vol. 95 (1981).
Encylopedia of Chemical Technology, by Kirk-Othmer, Third Edition, 1978, vol. 4, John Wiley and Sons, pp. 561-569.

*Primary Examiner*—Alan Siegel
*Attorney, Agent, or Firm*—K. K. Brandes

[57] ABSTRACT

A process for purifying sulfolene-containing streams, which contain polysulfones as impurities, comprises contacting the sulfolene-containing streams with activated carbon. The thus purified sulfolene-containing streams can be hydrogenated to sulfolane, e.g., over a supported nickel catalyst.

21 Claims, No Drawings

PURIFICATION AND HYDROGENATION OF SULFOLENES

BACKGROUND OF THE INVENTION

This invention relates to a process for catalytically hydrogenating sulfolenes to sulfolanes. In another aspect, this invention relates to a process for hydrogenating sulfolenes to sulfolanes over a nickel catalyst. In a further aspect, this invention relates to treating sulfolenes so as to remove impurities which interfere with the subsequent catalytic hydrogenation of sulfolenes.

The catalytic hydrogenation of sulfolenes to sulfolanes is well known. Generally a supported nickel catalyst is employed. Also the removal of sulfur dioxide and other impurities from sulfolenes prior to the catalytic hydrogenation has been taught, such as in U.S. Pat. Nos. 3,345,384 and 4,286,099. However, there is an ever present need to develop new, more effective processes for removing impurities from sulfolenes and for hydrogenating sulfolenes.

SUMMARY OF THE INVENTION

It is an object of this invention to provide an improved process for hydrogenating sulfolenes. It is another object of this invention to provide a method of purifying sulfolenes so as to remove therefrom small amounts of compounds which can act as catalyst poisons in the catalytic hydrogenation of sulfolenes. Further objects and advantages will become apparent from the following description and appended claims.

In accordance with this invention, a process for purifying sulfolenes comprises the step of contacting a sulfolene-containing feed stream, which also contains catalyst poisons for hydrogenation catalysts (preferably nickel-containing catalysts), with activated carbon, at such a weight ratio of activated carbon to the sulfolene-containing feed stream and under such conditions as to obtain a sulfolene-containing stream having reduced concentration of these catalyst poisons.

Any suitable weight ratio of activated carbon to sulfolene-containing stream may be used. The preferred weight ratio of activated carbon to the sulfolene-containing stream is at least about 1:100 and more preferably is in the range of from about 1:100 to about 10:100. The preferred sulfolene is beta-sulfolene, also referred to as 3-sulfolene.

Also in accordance with this invention, a process for hydrogenating sulfolenes comprises the steps of:

(a) contacting a sulfolene-containing feed stream, which also contains catalyst poisons for hydrogenation catalysts (preferably nickel-containing catalysts), with activated carbon, at such a weight ratio of activated carbon to the sulfolene-containing feed stream and under such conditions as to obtain a sulfolene-containing stream having reduced concentration of these catalyst poisons; and (b) contacting the sulfolene-containing stream obtained in step (a) having a reduced level of said catalyst poisons with a free hydrogen containing gas and a hydrogenation catalyst (preferably a supported nickel catalyst), under such hydrogenation conditions as to convert at least a portion of sulfolene to sulfolane.

In a preferred embodiment, the process for purifying sulfolenes and the process for hydrogenating sulfolenes comprise the additional step of passing a gas through a sulfolene-containing stream so as to remove at least a portion of dissolved sulfur dioxide therefrom. This additional step can be carried out before or after (preferably before) the step of contacting the sulfolene-containing feed stream with activated carbon.

In another preferred embodiment, the process for purifying sulfolenes and the process for hydrogenating sulfolenes comprise the additional step of contacting a sulfolene-containing stream with hydrogen peroxide under such conditions as to reduce the amount of dissolved sulfur dioxide in said sulfolene-containing stream. This step preferably is generally carried out after the step of contacting the sulfolene-containing feed stream with activated carbon (and if applicable, before the hydrogenation step).

DETAILED DESRIPTION OF THE INVENTION

The term "sulfolene" (sometimes also referred to as "sulfolenes" and "sulfolene compounds") as employed herein is defined in U.S. Pat. No. 3,622,598, herein incorporated by reference. This term includes substituted and unsubstituted 3-sulfolenes and 2-sulfolenes. The preferred sulfolene compound employed in this invention is unsubstituted 3-sulfolene (beta-sulfolene) which is commercially available and is produced by reaction of 1,3-butadiene and sulfur dioxide. The terms "sulfolane" or "sulfolane compounds" are also defined in U.S. Pat. No. 3,622,598.

The term "activated carbon" (sometimes also referred to as "charcoal") as used herein refers to any material consisting essentially of elemental carbon and having an internal surface area of at least about 300 $m^2/g$, generally up to about 10,000 $m^2/g$. Generally the activated carbon material is obtained by destructive distillation of carbonaceous materials such as wood, nut shells, rice hulls, animal bones, peat, lignite, tars and the like and subsequent heating to about 800°–1000° C. with steam or carbon dioxide or any other suitable gas. However, the method by which the activated carbon or charcoal employed in the processes of this invention is produced is not considered critical.

The activated carbon or charcoal material can be applied as irregularly shaped particles or as granules, pellets, fibers and the like. Physical properties of typical activated carbon grades and other pertinent information on activated carbon are given in Kirk-Othmer's "Encyclopedia of Chemical Technology", Third Edition, Volume 4, 1978, John Wiley and Sons, Inc., pages 561–569, herein incorporated by reference. The presently preferred activated carbon employed in the process of this invention has a surface area (as determined by the BET/$N_2$ method, ASTM D3037) in the range of from about 500 to about 5,000 $m^2/g$ and a pore volume (as determined by mercury porosimetry at 60 Kpsig) in the range of from about 0.4 to about 1.0 cc/g. Many of these activated carbon materials are commercially available as water-treating materials.

Any suitable sulfolene-containing feed stream can be employed in the process of this invention. This stream may be substantially undiluted raw sulfolene or it may be a solution of sulfolene in a suitable solvent such as an aqueous solution of a sulfolene (preferably beta-sulfolene). Preferably an aqueous solution comprising from about 40 to about 90 weight-% sulfolene (more preferably beta-sulfolene) is employed.

The process of this invention is directed to the removal of any poison for hydrogenation catalysts (preferably nickel-containing catalysts) from the sulfolene-containing feed stream. The most common catalyst poisons contained in sulfolene-containing streams are sulfur dioxide and polysulfones, especially those polysulfones having the repeat unit of [—$C_4H_6SO_2$—) and having been formed as by-products in the preparation of beta-sulfolene from butadiene and $SO_2$. The polysulfones are believed to decompose on the surface of hydrogenation catalysts, especially nickel catalysts, with generation of sulfur dioxide, which has long been recognized as a poison for catalysts employed in the hydrogenation of sulfolenes.

The sulfolene-containing feed stream and the activated carbon can be contacted in any suitable manner in any suitable apparatus, either in a batch process or in a continuous process. In a batch process, the sulfolene-containing feed stream and the activated carbon can be charged simultaneously or separately in any order to a vessel and mixed therein. The formed mixture is generally agitated for a time sufficient to reduce the amount of catalyst poisons to a desired level, perferably for a time in the range of from about 5 minutes to about 1 hour. The contacting temperature should be above the melting point of the sulfolene but below its decomposition temperature. This contacting can be carried out at near ambient conditions (such as 35°–50° C., 1 atm; presently preferred), or at elevated pressure and temperature conditions at which the sulfolene is stable.

The sulfolene-containing stream, formed in the process of this invention having a reduced content of catalyst poisons, can be separated from the activated carbon (containing absorbed catalyst poisons) by any suitable separation means (such as filtration, centrifugation, settling of activated carbon and draining of supernatant liquid) before this sulfolene-containing stream is processed further (such as in a catalytic hydrogenation process). However, it is within the scope of this invention to hydrogenate a sulfolene-containing stream having a reduced level of catalyst poisons and containing dispersed activated carbon particles, i.e., to hydrogenate sulfolene without prior separation of the sulfolene-containing stream and activated carbon dispersed therein.

In a continuous operation, the sulfolene-containing stream is generally passed through a fixed bed of activated carbon at a flow rate suitable for sufficient removal of catalyst poisons, generally at such elevated temperature/pressure conditions as discussed above. Generally the flow rate of the sulfolene-containing feed stream can range from about 0.5 to about 10 cc feed stream per cc activated carbon per hour.

Once the activated carbon has been saturated with absorbed poisons and has become ineffective as a catalyst-removing agent, the thus deactivated carbon can be discarded or can be regenerated, e.g., by heating in steam or in another suitable gas atmosphere at a temperature high enough (such as 800°–1000° C.) to cause substantial desorption of absorbed catalyst poisons.

In a preferred embodiment, a gas such as oxygen, nitrogen, air, helium, argon and the like is introduced near the bottom of a vessel containing the sulfolene-containing stream and bubbled through the sulfolene-containing stream so as to sweep out a portion of dissolved sulfur dioxide and also probably some butadiene. The optimal flow rate of the introduced gas greatly depends on the amount of the sulfolene-containing stream, the concentration of $SO_2$ in the sulfolene-containing stream, the desired rate of $SO_2$ removal, and the configuration of reactor and gas inlet means. Generally the above-described purging with a gas is carried out for a time period ranging from about 1 minute to about 1 hour.

In another preferred embodiment, hydrogen peroxide is added to a sulfolene-containing stream that has been contacted with activated carbon (either before or after separation of activated carbon and sulfolene-containing stream having reduced level of poisons). Generally enough $H_2O_2$ is added to the sulfolene-containing stream with stirring to give an electrical potential of this stream against a Pt/Ag-AgCl reference electrode of about 400–600 millivolts. The time of this treatment with $H_2O_2$ generally ranges from about 10 minutes to about 1 hours.

Processes for hydrogenating sulfolenes, e.g., in the presence of a nickel containing hydrogenation catalyst such as Raney nickel, and for recovering sulfolanes from the reaction mixture have been described in U.S. Pat. Nos. 3,152,144, 3,417,103 and 4,286,099, herein incorporated by reference. Presently preferred hydrogenation conditions include a Raney catalyst, an initial hydrogen pressure of about 400–2000 psig, a reaction temperature of about 100°–200° F., and a reaction time ranging from about 10 minutes to about 5 hours.

The following examples are presented to further illustrate this invention without unduly limiting the scope of this invention.

EXAMPLE

This example illustrates the pretreatment of 3-sulfolene (beta-sulfolene) in according with this invention and the subsequent catalytic hydrogenation of 3-sulfolene to sulfolane.

All runs employed as feed crude 3-sulfolene, which was manufactured in the Philtex Plant of Phillips 66 Company in Borger, Tex. The crude 3-sulfolene was mixed with distilled water so as to give aqueous solutions containing 52.6 weight-% 3-sulfolene. Air was passed through the obtained turbid-looking aqueous solution of 3-sulfolene for about 10 minutes at about 100° F. In several runs, about 1–5 g Nuchar ® activated carbon (provided by Westvaco Corporation Chemical Division, Covington. VA) was added with stirring to about 100–200 grams of the aqueous 3-sulfolene solution having a pH of about 2.5–3.0. Nuchar ® activated carbon had a pore volume (determined by mercury porosimetry at 60 Kpsi) of 0.64 cc/g, a surface area (determined by the BET/$N_2$ method; ASTM D3037) of 930 $m^2$/g and a calculated average pore diameter of 27 angstroms.

To the aqueous, air-purged solution of 3-sulfolene, either with or without dispersed Nuchar ®, was added enough of an aqueous 10 weight-% $H_2O_2$ solution (generally about 20 drops) to give a potential of 500±30 millivolts against a normal Pt/Ag-AgCl reference electrode. The aqueous solution of 3-sulfolene and $H_2O_2$ (plus, optionally, Nuchar ®) was stirred for about 20–90 minutes.

The Nuchar ® activated carbon, when added, was allowed to settle, and the supernatant aqueous solution of 3-sulfolene and hydrogen peroxide was decanted and added to a nitrogen-purged 300 mL autoclave. About 1–2 grams of wet Raney nickel catalyst (obtained from Strem Chemicals, Inc., Newburyport, MA) was added to the autoclave reactor which was then pressured with hydrogen gas to about 1,000 psig. The reactor contents were stirred and heated to about 110° F. (range: 106°–126° F.). The drop in hydrogen pressure (due to hydrogen consumption in the hydrogenation reaction)

was generally determined at 5-10 minute time intervals. Generally, when the pressure had dropped to about 500 psig, the autoclave was repressured to about 1,000 psig once or several times. The total cumulative drop in hydrogen pressure (a measure of total hydrogen consumption) was calculated for each run. A particular hydrogenation run was considered completed when the reaction pressure remained essentially constant for about 10 minutes. The completion of the hydrogenation reaction was either due to the hydrogenation of all available sulfolene or was due to catalyst deactivation. Pertinent test data are summarized in Table I.

TABLE I

| Run | Weight of Sulfolene Solution (g) | Weight of Activated Carbon Added (g) | Weight Ratio of Activ. C to Sulfolene Solution | Hydrogenation of 3-Sulfolene | | | |
|---|---|---|---|---|---|---|---|
| | | | | Weight of Catalyst (g) | Cummulative Press. Drop (psig) | Total Run Time (minutes) | Psig Drop Per Minute | Total Psig Drop per g Sulfolene Solution |
| 1 | 155 | 0 | 0 | 1.55 | 1355 | 219 | 6.2 | 8.7 |
| 2 | 157 | 0 | 0 | 1.57 | 1285 | 226 | 5.7 | 8.2 |
| 3 | 146 | 1.25 | 0.9:100 | 1.46 | 1275 | 250 | 5.1 | 8.7 |
| 4 | 153 | 2.5 | 1.6:100 | 1.53 | 1812 | 232 | 7.8 | 11.8 |
| 5 | 175 | 5.0 | 2.9:100 | 1.75 | 2165 | 100 | 21.7 | 12.4 |
| 6 | 169 | 5.0 | 3.0:100 | 1.69 | 2110 | 74 | 28.5 | 12.5 |
| 7 | 170 | 5.0 | 2.9:100 | 1.70 | 2200 | 129 | 17.1 | 12.9 |
| 8 | 150 | 5.0[1] | 3.3:100[1] | 1.50 | 1770 | 116 | 15.3 | 12.4 |
| 9 | 157 | 5.0[2] | 3.2:100[2] | 1.57 | 1895 | 153 | 12.4 | 12.1 |
| 10 | 180 | 5.0[3] | 2.8:100[3] | 1.79 | 2355 | 189 | 12.5 | 13.1 |
| 11 | 115 | 5.0[4] | 4.3:100 | 1.10 | 1080 | 250 | 4.3 | 9.4 |

[1]The same activated carbon charge was employed in previous run 7; thus the weight ratio of activated carbon to sulfolene solution in the combination of runs 7 and 8 was 1.6:100.
[2]The same activated carbon charge was employed in previous runs 7 and 8; thus the weight ratio of activated carbon to sulfolene solution in the combination of runs 7,8 and 9 was 1.0:100.
[3]The same activated carbon charge was employed in previous runs 7,8 and 9; thus the weight ratio of activated carbon to sulfolene solution of the combination of runs 7, 8, 9 and 10 was 0.8:100.
[4]The same activated carbon charge was employed in previous runs 7, 8, 9 and 10; obviously the activated carbon was substantially saturated with catalyst poisons and was no longer effective as poison removal agent.

Data in Table I clearly show that, at a weight ratio of activated carbon to the sulfolene solution of about 1:100 to about 4:100, the pretreatment of the aqueous sulfolene solution (containing 52.6 weight-% 3-sulfolene) at the experimental conditions employed in this example resulted in a significantly enhanced rate of the subsequent hydrogenation (as measured by psig drop per minute) and to a greater degree of completion of the hydrogenation (as measured by total psig drop per gram sulfolene solution). Further calculations indicated that in invention runs 4-10 the hydrogenation was approximately 100%, whereas in control runs 1 and 2 the degree of hydrogenation was only about 60-75%. Since the sulfolene solution contained 52.6 weight-% 3-sulfolene, the preferred weight ratio of activated carbon to sulfolene solution of about 1:100 to about 4:100 corresponds to a weight ratio of activated carbon to 3-sulfolene of about 2:100 to about 8:100.

Even though run 3 did not show an improvement in rate and degree of hydrogenation vs. control runs 1 and 2, the data in sequential runs 7-10 indicate that a weight ratio of activated carbon to sulfolene solution as low as 0.8 can be effective when longer contact times are employed. It is believed that even smaller weight ratios than 0.8 could be effective in a more efficient contacting operation than employed in tests of this example, e.g., by passing the sulfolene-containing feed stream through a fixed bed of activated carbon. Also, feed streams having lower concentrations of catalyst poisons and activated carbon having higher surface areas than those employed in tests of this example could make it possible to treat sulfolene-containing feeds at weight ratios of activated carbon to sulfolene-containing feed stream lower than about 0.8 and to attain an improvement in rate and degree of hydrogenation.

Reasonable variations and modifications are possible within the scope of this disclosure without departing from the spirit and scope of this invention.

That which is claimed is:

1. A process comprising the step of (a) contacting a sulfolene-containing feed stream, which also contains polysulfones as impurities with activated carbon at a weight ratio of said activated carbon to said sulfolene-containing feed stream of at least about 1.6:100 and under such conditions as to obtain a sulfolene-containing stream having reduced concentration of said polysulfones.

2. A process in accordance with claim 1, wherein the weight-ratio of said activated carbon to said sulfolene-containing feed stream is in the range of from about 1.6:100 to about 10:100.

3. A process in accordance with claim 1, wherein said sulfolene-containing feed stream comprises 3-sulfolene.

4. A process in accordance with claim 3, wherein the weight ratio of activated carbon to 3-sulfolene contained in said sulfolene-containing feed stream is in the range of from about 2:100 to about 8:100.

5. A process in accordance with claim 4, wherein said sulfolene-containing feed stream is an aqueous solution of 3-sulfolene.

6. A process in accordance with claim 1, wherein said polysulfones comprise at least one polysulfone having the repeat unit of $[-C_4H_6SO_2-]$.

7. A process in accordance with claim 1, wherein said sulfolene-containing feed stream additionally contains sulfur dioxide.

8. A process in accordance with claim 1, wherein said activated carbon has a surface area in the range of from about 500 to about 5,000 $m^2/g$ and a pore volume of from about 0.4 to about 1.0 cc/g.

9. A process in accordance with claim 7, wherein prior to said contacting of the sulfolene-containing feed stream with activated carbon, a gas is passed through said sulfolene-containing feed stream so as to remove at least a portion of dissolved sulfur dioxide therefrom.

10. A process in accordance with claim 1, wherein said sulfolene-containing feed stream additionally contains sulfur dioxide, and said process comprises the additional step, being carried out after said contacting step (a), of adding hydrogen peroxide to said sulfolene-containing stream having reduced concentration of said polysulfones, in such amount and under such conditions as to reduce the amount of sulfur dioxide dissolved in said sulfolene-containing stream having reduced concentration of said polysulfones.

11. A process in accordance with claim 10, wherein the amount of hydrogen peroxide is such as to give an electrical potential of said sulfolene-containing stream having reduced concentration of catalyst poisons against a Pt/Ag-ACl reference electrode of about 400–600 millivolts.

12. A process in accordance with claim 1 further comprising the step of separating activated carbon from the sulfolene-containing stream having reduced concentration of said polysulfones.

13. A process in accordance with claim 1 comprising the additional step of (b) contacting the sulfolene-containing stream having reduced concentration of said polysulfones obtained in step (a) with a free hydrogen containing gas and a hydrogenation catalyst, under such hydrogenation conditions as to convert at least a portion of sulfolene to sulfolane.

14. A process in accordance with claim 13, wherein said sulfolene-containing stream comprises 3-sulfolene.

15. A process in accordance with claim 13, wherein the hydrogenation catalyst employed in step (b) is a nickel-containing catalyst.

16. A process in accordance with claim 15, wherein said nickel containing catalyst is Raney nickel.

17. A process in accordance with claim 16, wherein said hydrogenation conditions comprise an initial hydrogen pressure in the range of from about 500 to about 2,000 psig, a reaction temperature in the range of from about 100° to about 200° C. and a reaction time in the range of from about 10 minutes to about 5 hours.

18. A process in accordance with claim 13, wherein prior to said contacting step (a) a gas is passed through said sulfolene-containing feed stream, which comprises dissolved sulfur dioxide, so as to remove at least a portion of dissolved sulfur dioxide therefrom.

19. A process in accordance with claim 13 comprising the additional step, being carried out after step (a) and before step (b), of adding hydrogen peroxide to the sulfolene-containing stream obtained in step (a), which also contains dissolved sulfur dioxide, in such amounts and under such conditions as to reduce the amount of sulfur dioxide dissolved in said sulfolene-containing stream having reduced concentration of polysulfones.

20. A process in accordance with claim 13 comprising the additional step of separating activated carbon from said sulfolene-containing stream having reduced concentration of polysulfones before hydrogenation step (b).

21. A process in accordance with claim 13, wherein sulfolane formed in step (b) is recovered from the reaction mixture obtained in step (b).

* * * * *